United States Patent
Toyama et al.

(10) Patent No.: US 10,472,312 B2
(45) Date of Patent: Nov. 12, 2019

(54) METHOD FOR PRODUCING PHENOXYETHANOL DERIVATIVE

(71) Applicant: SHIONOGI & CO., LTD.[, Osaka (JP)

(72) Inventors: Takayuki Toyama, Hyogo (JP); Naoki Miyake, Hyogo (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 16/085,110

(22) PCT Filed: Mar. 14, 2017

(86) PCT No.: PCT/JP2017/010159
§ 371 (c)(1),
(2) Date: Sep. 14, 2018

(87) PCT Pub. No.: WO2017/159669
PCT Pub. Date: Sep. 21, 2017

(65) Prior Publication Data
US 2019/0084910 A1    Mar. 21, 2019

(30) Foreign Application Priority Data
Mar. 15, 2016    (JP) .................................. 2016-050604

(51) Int. Cl.
*C07C 41/26*    (2006.01)
*A61K 31/085*    (2006.01)

(52) U.S. Cl.
CPC ............ *C07C 41/26* (2013.01); *A61K 31/085* (2013.01)

(58) Field of Classification Search
CPC ............................. C07C 41/26; A61K 31/085
See application file for complete search history.

(56) References Cited

U.S. PATENT DOCUMENTS

| | | | |
|---|---|---|---|
| 3,836,539 A | 9/1974 | Boesch | |
| 4,982,016 A * | 1/1991 | Choi | C07C 29/147 568/811 |
| 5,578,742 A | 11/1996 | Metzler et al. | |
| 2012/0053341 A1 | 3/2012 | Chopra | |

FOREIGN PATENT DOCUMENTS

| | | | |
|---|---|---|---|
| CN | 103242142 | 8/2013 | |
| CN | 104030896 | 9/2014 | |
| EP | 2236494 | 10/2010 | |
| JP | 48-39639 | 6/1973 | |
| JP | 05-271130 | 10/1993 | |
| JP | 07509222 | 10/1995 | |
| JP | 7-316131 | 12/1995 | |
| JP | 07316131 A * | 12/1995 | ............ C07C 41/01 |
| JP | 8-511793 | 12/1996 | |
| JP | H10502924 | 3/1998 | |
| JP | 11-310556 | 11/1999 | |
| JP | 2007517796 | 7/2007 | |
| JP | 2010-502696 | 1/2010 | |
| JP | 2010518150 | 5/2010 | |
| JP | 2013-517320 | 5/2013 | |
| JP | 2013-224263 | 10/2013 | |
| WO | WO8605777 | 3/1986 | |
| WO | WO1996002486 | 2/1996 | |
| WO | WO0136360 | 5/2001 | |
| WO | WO2005063701 | 7/2005 | |
| WO | WO2008030119 | 3/2008 | |

(Continued)

OTHER PUBLICATIONS

LiBH4(NaBH4)/Me3SiCl, an Unusually Strong and Versatile Reducing Agent Authors: Giannis, et al Publication data: Angew. Chem. Int. Ed. Engl., Feb. 1, 1989 Source info: vol. 28, Nr: 2, pp. 218-220.
In vitro and in vivo biologic effects of Ospemifene (FC-1271a) in breast cancer Authors: Taras T L, et al Publication data: Journal of Steroid Biochemistry and Molecular Biology,,Jun. 1, 2001,Elsevier Science LTD., Oxford, GB Source info: vol. 77, Nr: 4-5, pp. 271-279.
Lukác, I. et al., "Synthesis of acyl 1-acetoxy-2-phenoxyethanes and the corresponding hydroxy derivatives", Collection Czechoslov. Chem. Commun., (1980), vol. 45, No. 6.
Suarez, A.G., "AlCl3-DMA reagent in the regioselective solvent free Friedel-Crafts acylation reaction of benzodioxin derivatives", Tetrahedron Letters, (Apr. 30, 1999), vol. 40, No. 18.

(Continued)

*Primary Examiner* — Rosalynd A Keys
(74) *Attorney, Agent, or Firm* — Sullivan & Worcester LLP

(57) ABSTRACT

Provided is a method for producing a phenoxyethanol derivative. This method for producing a compound represented by formula (II) is characterized in that a compound represented by formula (I) (in the formula, R1 is a substituted or unsubstituted alkyl) is reduced in the presence of lithium borohydride.

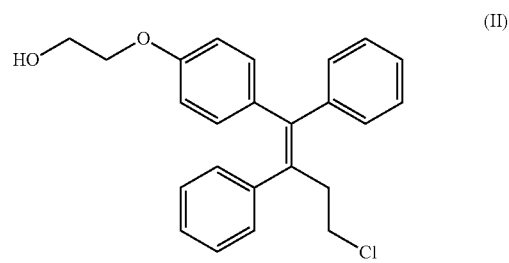

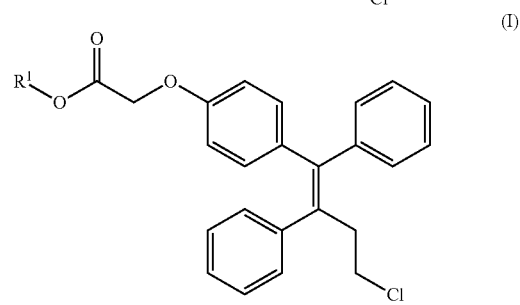

6 Claims, No Drawings

(56) References Cited

FOREIGN PATENT DOCUMENTS

| WO | WO2008099059 | 8/2008 |
|---|---|---|
| WO | WO2009081789 | 7/2009 |
| WO | WO2011089385 | 7/2011 |
| WO | WO2012023582 | 2/2012 |
| WO | WO2012089606 | 7/2012 |
| WO | WO2012089607 | 7/2012 |
| WO | WO2014060639 | 4/2014 |
| WO | WO2014060640 | 4/2014 |
| WO | WO2016043189 | 3/2016 |
| WO | WO2016110805 | 7/2016 |

OTHER PUBLICATIONS

Rele, S.M. et al., "Salt/ligand-activated low-valent titanium formulations: the 'salt effect' on diastereoselective carbon-carbon bond forming SET reactions", Tetrahedron, vol. 64, No. 30-31, 2008.

Zhang, D. et al., "Two-step synthesis technology of ospemifene", Xiandai Yaowu Yu Linchuang—Drugs & Clinic, Tainjin Zhongcaoyao Zazhishe, CN, (Mar. 29, 2012), vol. 27, No. 4.

Bonaccini,C. et al, Synthesis, Biological Evaluation and Docking Studies of Casuarine Analogues: Effects of Structural Modifications at Ring B on Inhibitory Activity Towards Glucoamylase, European Journal of Organic Chemistry, 2010, No. 29, p. 5574-5585, Supporting Information, Scheme 7, Supporting Information 22a, paragraph of synthesis.

Mayer,S.C. et al, Discovery of Begacestat, Nothch-I-Sparing y-Secretase Inhibitor for the Treatment of Alzheimer's Disease, Journal of 1-7,12,13 Medicinal Chemistry, 2008, vol. 51, No. 23, p. 1348-7351, Scheme 1.

Drew,M.G.B. et al, Synthesis of disaccharides containing a-linked G1cNAc or (3-linked ManNAc units, Tetrahedron, 2001, vol. 57, No. 37, 1-7,12,13 p. 7919-7937, Scheme 9, 4.Experimental(4.6).

Jordi Robles, 2-(4-Acetyl-1-nitrophenyl)ethyl: A New Base-Labile Carboxyl Protecting Group. Synthesis, Dec. 1993, 1261-1266.

N. Balu, Influence of External Ligands and Auxiliaries on the Reactivity of Low-Valent Titanium in McMurry Reaction: Selectivity and Mechanistic Profile. J. Am. Chem. Soc. (1996), 118, 5932-5937.

Shyam M. Rele, Salt/ligand-activated low valent titanium formulations: the 'salt effect' on disastereoselective carbon-carbon bond forming SET reactions. Tetrahedron. 64 (2008) 7225-7233.

International Search Report for WO2016/043189 (PCT/JP[2015/076165) dated Dec. 8, 2015.

International Preliminary Report on Patentability and Written Opinion for WO2016/043189 (PCT/JP[2015/076165) dated Mar. 21, 2017.

International Search Report for WO2017/159669 (PCT/JP2017/010159) dated Sep. 21, 2017.

International Preliminary Report on Patentability and Written Opinion for WO2017/159669 (PCT/JP2017/010159) dated Sep. 18, 2018.

* cited by examiner

METHOD FOR PRODUCING PHENOXYETHANOL DERIVATIVE

An English language translation of the original Japanese specification from PCT/JP2017/010159 is submitted herewith. Please replace the original specification with the provided English language specification.

TECHNICAL FIELD

The present invention relates to a production method for phenoxyethanol derivatives. More specifically, the invention relates to a production method for the selective estrogen receptor modulator ospemifene. Furthermore, in a separate aspect, the present invention relates to a production method for alcohols characterized in that ester is reacted with lithium borohydride.

BACKGROUND ART

Patent literatures 1 through 5 describe a production method for the selective estrogen receptor modulator ospemifene represented by the formula (II):

(Chemical formula 1)

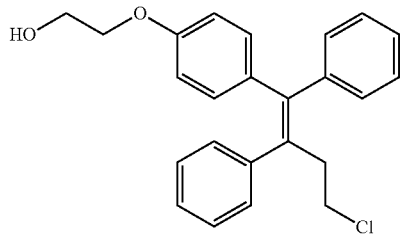

(II)

Patent literature 1 describes a production method for obtaining ospemifene, wherein 4-hydroxybenzophenone and 3-chloropropiophenone are subjected to McMurry reaction to obtain the formula:

(Chemical formula 2)

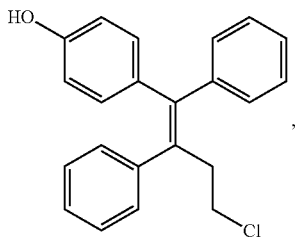

, the obtained compound is alkylated with an alkylation agent represented by the formula: X—(CH$_2$)$_2$—O—Pr (wherein X is Cl, Br, I, methyloxy or tosyloxy, and Pr is a protective group) to obtain the formula:

(Chemical formula 3)

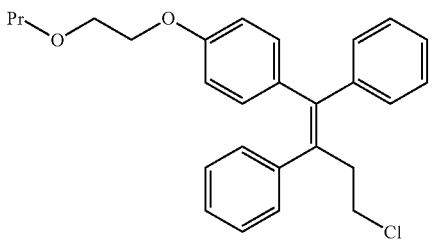

, which is then deprotected; and a production method for obtaining ospemifene wherein alkylation is performed with an alkylation agent represented by the formula: X—CH$_2$—COOR (wherein X is Cl, Br, I, methyloxy or tosyloxy, and R is alkyl) to obtain the compound represented by the formula:

(Chemical formula 4)

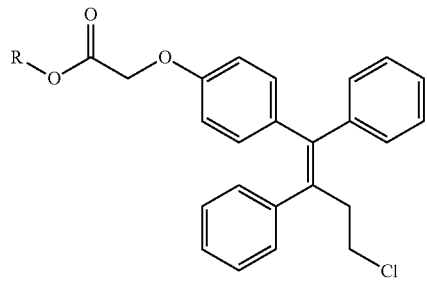

, and then reducing this ester.

Patent literature 2 describes a production method for obtaining ospemifene through a McMurry reaction from a compound represented by the formula:

(Chemical formula 5)

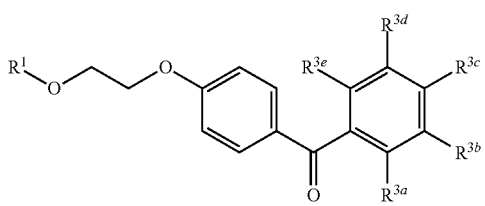

(wherein R$^1$ represents H or C1-6 alkyl optionally substituted with one or multiple —OH groups, and R$^{3a}$, R$^{3b}$, R$^{3c}$, R$^{3d}$ and R$^{3e}$ each independently represent H or —OH) and a compound represented by the formula:

(Chemical formula 6)

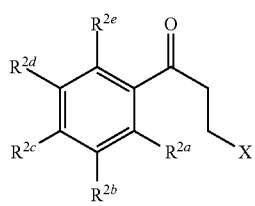

(wherein X represents halogen or —OH, and R$^{2a}$, R$^{2b}$, R$^{2c}$, R$^{2d}$ and R$^{2e}$ each independently represent H or —OH).

Patent literature 3 describes a production method for obtaining ospemifene wherein the formula:

(Chemical formula 7)

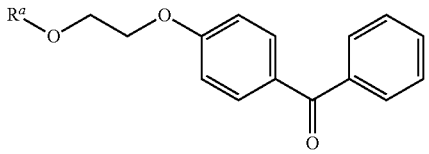

(wherein $R^a$ is C(O)—$R^b$, where $R^b$ is optionally substituted phenyl) and 3-chloropropiophenone are subjected to McMurry reaction to obtain the formula:

(Chemical formula 8)

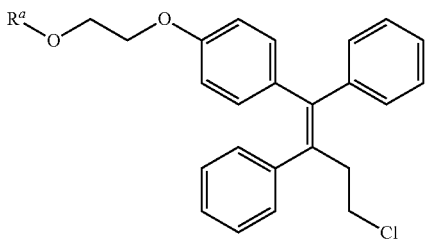

(wherein the symbols have the same meaning as above), which is then deprotected.

Patent literature 4 describes a production method for obtaining ospemifene, wherein a compound represented by the formula:

(Chemical formula 9)

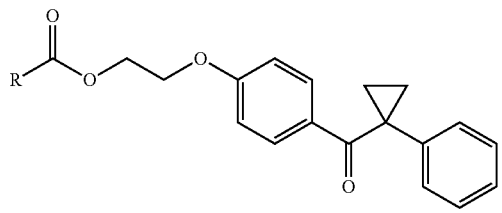

and phenyl magnesium halide are reacted to obtain a compound represented by the formula:

(Chemical formula 10)

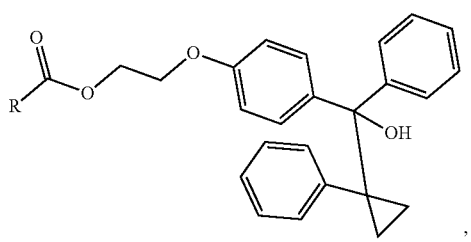

which is treated with hydrochloric acid to obtain the formula:

(Chemical formula 11)

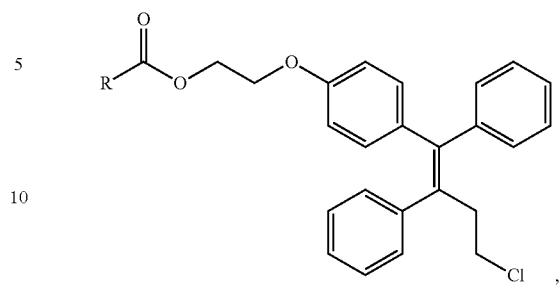

which is then deprotected.

Patent literature 5 describes a production method for obtaining ospemifene characterized in that a perfluorophenyl group is introduced.

Furthermore, the method of producing alcohols by reacting ester and lithium borohydride is widely known.

However, patent literatures 1 through 5 do not describe or suggest a production method for ospemifene using reduction reaction by means of lithium borohydride. Furthermore, in the case of methods of producing alcohols by reacting ester and lithium borohydride, reacting in the presence of borane or reacting in the presence of trimethylsilyl chloride is not known.

PRIOR ART LITERATURES

Patent Literatures

Patent literature 1: International Publication No. 2008/099059 pamphlet
Patent literature 2: International Publication No. 2011/089385 pamphlet
Patent literature 3: International Publication No. 2014/060640 pamphlet
Patent literature 4: International Publication No. 2014/060639 pamphlet
Patent literature 5: Chinese Application Publication No. 103242142 pamphlet

SUMMARY OF THE INVENTION

Problem to be Solved by the Invention

It is an object of the present invention to provide a novel useful production method for phenoxyethanol derivatives represented by formula (II). Furthermore, it is an object of the present invention to provide a method of producing alcohols by reacting ester and lithium borohydride, wherein the production of byproducts is suppressed.

Means for Solving the Problem

The production method described in embodiment example 7 of patent literature 1 is a method of producing ospemifene by reducing (4-(4-chloro-1,2-diphenyl-but-1-enyl)-phenoxy-acetic acid ethyl ester with lithium aluminum hydride. This production method has a poor yield of 43% and uses lithium aluminum hydride, which is an explosive reagent.

The production method described in embodiment examples 1A and 1B of patent literature 2 is a method of producing ospemifene means of a McMurry reaction of 4-(2-hydroxyethoxy)benzophenone and 3-chloropropiophenone.

The production method described in embodiment example 11 of patent literature 3 is a method of producing ospemifene by reducing (Z)-(2-(4-(4-chloro-1,2-diphenyl-but-1-enyl)phenoxy)ethyl pivalate with lithium aluminum hydride. However, this production method has a poor yield of 61% and uses lithium aluminum hydride, which is an explosive reagent.

The method of embodiment example 2 of International Application No. PCT/JP2015/076165 is a method of producing ospemifene by reducing (Z)-2-(4-(4-chloro-1,2-diphenyl-but-1-enyl)phenoxy)methyl benzoate with sodium borohydride in the presence of methanol. In this method, during reaction, sodium borohydride reacts with methanol to produce hydrogen, so large scale production involves the risk of explosion.

Furthermore, in the case of common reduction reaction using sodium borohydride or the like, it is difficult to control the production of hydrogen in the reduction reaction and the heat of reaction, so this reduction method is not suitable for industrialization or other types of mass production.

The present inventors discovered that ospemifene can be efficiently produced by reducing a compound represented by the formula (I):

(Chemical formula 12)

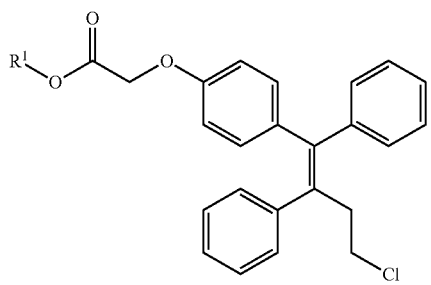

(I)

(wherein $R^1$ is a substituted or unsubstituted alkyl) using lithium borohydride as a reducing agent.

Furthermore, the present inventors discovered that in the method of producing alcohols by reacting ester with lithium borohydride, lithium hydroxide is produced through the reaction of lithium borohydride with moisture in the solvent or air, and this lithium hydroxide causes the esters to be hydrolyzed, leading to the production of carboxylic acid. The produced carboxylic acid cannot be readily reduced to alcohol with lithium borohydride and becomes a byproduct.

To solve this problem, it was discovered that alcohols can be efficiently produced by reducing the formed carboxylic acid to the corresponding alcohol by performing the ester reduction reaction in the presence of borane or in the presence of trimethylsilyl chloride.

This production method, unlike the known production methods described above, does not employ explosive reagents and has good yield and thus favorable cost of goods sold (COGS), and so is very well suited for industrial use.

Namely, the present invention relates to the following.

(1) A production methods for a compound represented by the formula (II):

(Chemical formula 14)

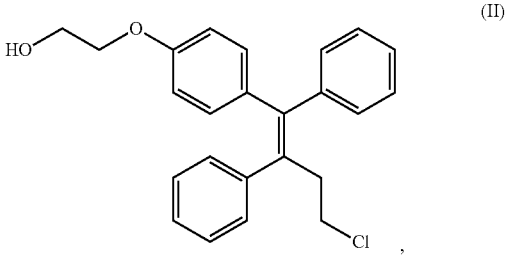

(II)

characterized in that a compound represented by the formula (I):

(Chemical formula 13)

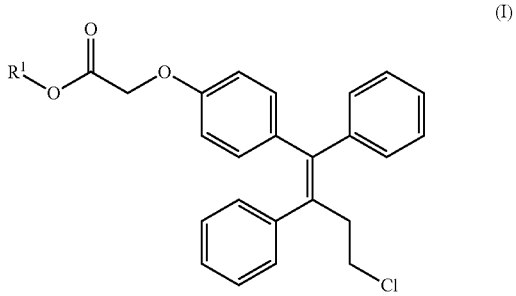

(I)

(wherein $R^1$ is a substituted or unsubstituted alkyl) is reduced in the presence of lithium borohydride.

(2) A production method as set forth under (1) above, characterized in that the lithium borohydride is formed in the reaction system.

(3) A production method as set forth under (2) above, characterized in that the lithium borohydride is formed in the reaction system by reacting potassium borohydride with lithium chloride.

(4) A production method as set forth under any one of (1) through (3) above, characterized in that the reaction is performed in the presence of borane.

(5) A production method as set forth under any one of (1) through (3) above, characterized in that the reaction is performed in the presence of trimethylsilyl chloride.

(6) A production method as set forth under any one of (1) through (5) above wherein $R^1$ is methyl.

(7) A production method as set forth under any one of claims 1 through 6, wherein the ratio between the compound represented by the formula (II):

(Chemical formula 15)

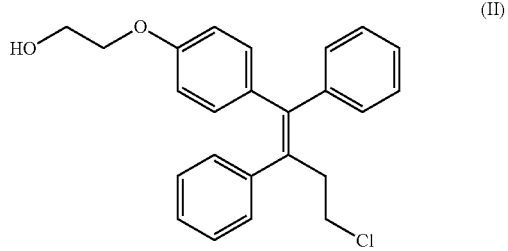

(II)

and the total of the compound represented by said formula (II) and the compounds represented by the formula (III):

(Chemical formula 16)

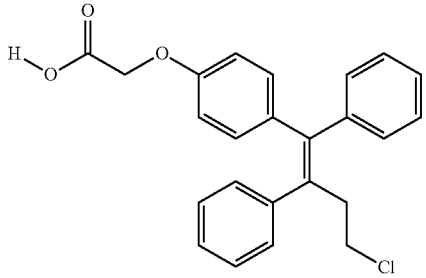

(III)

is 0.95≤(II)/((II)+(III))<1.

It should be noted that the compounds represented by formula (III) are byproducts.

(8) A production method for alcohols characterized in that ester and lithium borohydride are reacted in the presence of borane.

(9) A production method for alcohols characterized in that ester and lithium borohydride are reacted in the presence of trimethylsilyl chloride.

It should be noted that the alcohols of (8) and (9) signify alcohols that correspond to the ester.

(10) A production method as set forth under (8) or (9) above, characterized in that the lithium borohydride is formed in the reaction system.

(11) A production method as set forth under (10) above, characterized in that the lithium borohydride is formed in the reaction system by reacting potassium borohydride with lithium chloride.

(12) A reaction product wherein the ratio between the compound represented by the formula (II):

(Chemical formula 17)

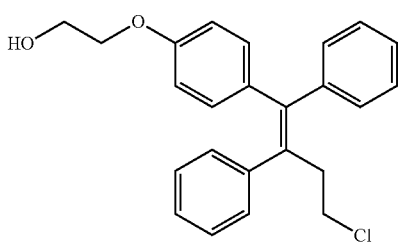

(II)

and the total of the compound represented by said formula (II) and the compounds represented by the formula (III):

(Chemical formula 18)

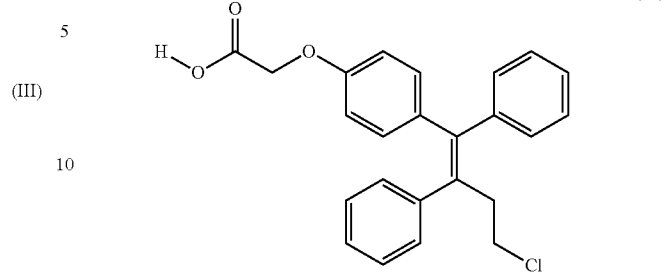

(III)

is 0.95≤(II)/((II)+(III))<1.

(13) A pharmaceutical composition containing a compound represented by the formula (II):

(Chemical formula 19)

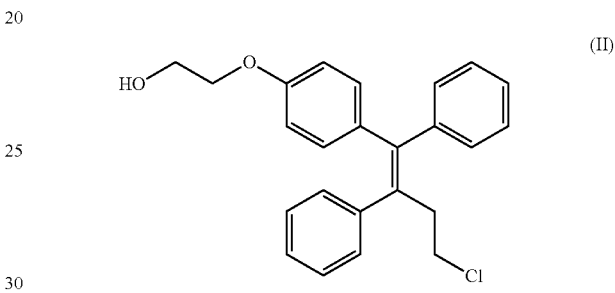

(II)

as an active ingredient and furthermore containing compounds represented by the formula (III):

(Chemical formula 20)

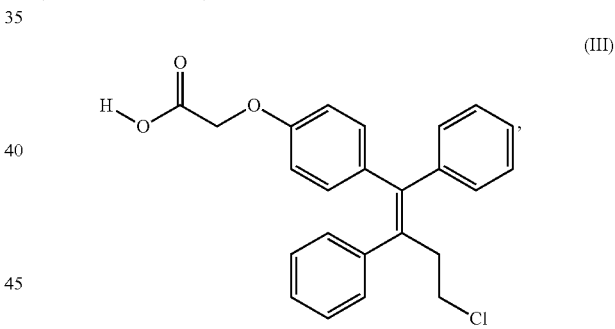

(III)

wherein the quantity of the compounds represented by said formula (III) is 0.2 weight percent or less of the quantity of the compound represented by said formula (II):

Effect of the Invention

Using the present invention makes it possible to efficiently produce phenoxyethanol derivatives represented by formula (II).

MODES FOR EMBODYING THE INVENTION

The terms used in the present specification are explained below.

"Halogen" includes fluorine, chlorine, bromine and iodine. Fluorine and chlorine are especially preferable.

"Alkyl" signifies straight chain or branched alkyl with 1 to 6 carbons. Alkyls with 1 to 4 carbons, alkyls with 1 to 3 carbons and the like are included. As examples, methyl, ethyl, n-propyl, isopropyl, n-butyl, isobutyl, sec-butyl, tert-butyl, n-pentyl, isopentyl, neopentyl, hexyl, isohexyl and the like may be mentioned.

Methyl is preferable as the alkyl in $R^1$.

Substituents of "substituted alkyl" include halogen, hydroxy, mercapto, nitro, nitroso, cyano, azido, formyl, amino, carboxy, alkyl, haloalkyl, alkenyl, alkynyl, non-aromatic carbocyclic groups, aromatic carbocyclic groups, aromatic heterocyclic groups, non-aromatic heterocyclic groups, substituted carbamoyl, substituted sulfamoyl, substituted amidino, groups represented by the formula: —O—$R^x$, groups represented by the formula: —O—C(=O)—$R^x$, groups represented by the formula: —C(=O)—$R^x$, groups represented by the formula: —C(=O)—O—$R^x$, groups represented the formula: —S—$R^x$ and groups represented by the formula: —$SO_2$—$R^x$ (here, $R^x$ is alkyl, haloalkyl, alkenyl, alkynyl, a non-aromatic carbocyclic group, aromatic carbocyclic group, aromatic heterocyclic group, non-aromatic heterocyclic group, carbamoyl, sulfamoyl or amidino). Any one or multiple substitutable positions may be substituted with these substituents.

Examples of substituents of the "substituted alkyl" in $R^1$ include hydroxy, alkyloxy (hydroxyalkyloxy, phenylalkyloxy, etc.), non-aromatic carbocyclic oxy (tetrahydropyranyloxy, etc.), alkyl carbonyloxy (methyl carbonyloxy, ethyl carbonyloxy, etc.), aromatic carbocyclic carbonyloxy (phenyl carbonyloxy, etc.), acyl (acetyl, trichloroacetyl, benzoyl, etc.), alkyloxy carbonyl (t-butoxycarbonyl, etc.), alkyl sulfonyl (methanesulfonyl, etc.), alkyloxyalkyl (methoxymethyl, etc.), trialkyl silyl (t-butyl dimethyl silyl, etc.), and the like. Hydroxy, alkyloxy, non-aromatic carbocyclic oxy, alkyl carbonyloxy, aromatic carbocyclic carbonyloxy and the like are preferable.

It should be noted that reacting a compound with another compound in the present specification includes reacting salts thereof or solvates thereof.

The production method of the present invention can be implemented, for example, as follows.

First Process (Chemical formula 21)

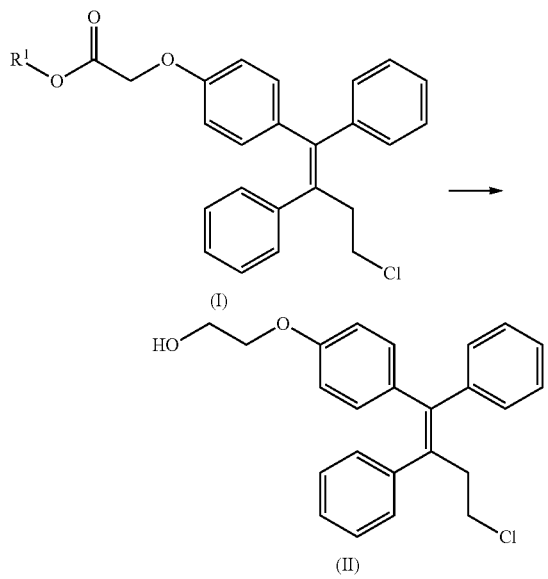

($R^1$ is a substituted or unsubstituted alkyl.)

This process involves reducing the compound represented by formula (I) in the presence of lithium borohydride to obtain the compound represented by formula (II).

Lithium borohydride is suitably reacted at a 0.3 mol equivalent to 5 mol equivalent quantity relative to the compound represented by formula (I).

It should be noted that "in the presence of lithium borohydride" includes the case of adding lithium borohydride as well as the case of forming lithium borohydride in the reaction system.

Lithium borohydride can be formed in the reaction system by reacting potassium borohydride or sodium borohydride with lithium chloride or lithium bromide.

This process makes it possible to produce the compound represented by formula (II) at a higher yield than with the methods described in patent literatures 1 and 3, which use other reducing agents.

The solvent is not particularly limited, so long as it allows the aforementioned process to proceed efficiently. One or more solvents selected from among toluene, cyclopentyl methyl ether, tetrahydrofuran, 2-methyl tetrahydrofuran, dimethyl sulfoxide and the like can be used.

The reaction temperature is not particularly limited, but normally, the reaction can be performed at approximately 0 to 100° C., or preferably at 0° C. to room temperature.

The reaction time is not particularly limited, but is usually 0.5 hours to 24 hours, or preferably, 1 to 10 hours.

It will be noted that the present inventors discovered that a compound represented by the formula (III):

(Chemical formula 22)

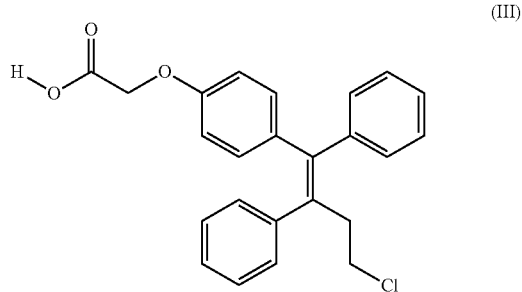

is formed as a byproduct in the above process. The present inventors also discovered a method of suppressing the formation of this byproduct. This is presented below.

In the above process, carboxylic acid formed the system can be reduced to alcohol by reacting in the presence of borane.

It should be noted that "in the presence of borane" includes the case of adding borane and the case of forming borane in the reaction system.

Borane can be formed by reacting lithium borohydride with a Lewis acid.

The borane is suitably reacted at 0.05 mol equivalents to 1 mol equivalent relative to the compound represented by formula (I). Here, 0.05 mol equivalents to 0.3 mol equivalents is preferable, and 0.05 mol equivalents to 0.15 mol equivalents is even more preferable.

Examples of the Lewis acid include chlorotrimethyl silane. The Lewis acid is suitably reacted at 0.05 mol equivalents to 1 mol equivalents at relation to the compound represented by formula (I). Here, 0.05 mol equivalents to 0.3 mol equivalents is preferable, and 0.05 mol equivalents to 0.15 mol equivalents is even more preferable.

The ratio between the compound represented by the formula (II):

(Chemical formula 23)

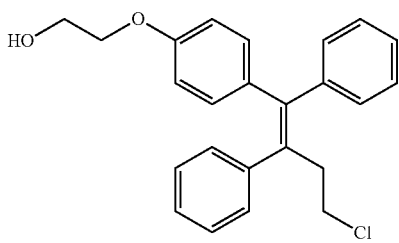
(II)

and the total of the byproduct compounds represented by the formula (III):

(Chemical formula 24)

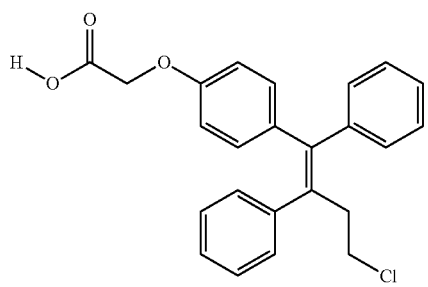
(III)

can be calculated through HPLC analysis on the basis of the area percentages (UV detection wavelength: 235 nm) of the compound represented by formula (II) and the compounds represented by formula (III).

Surface area percentage represents the surface area of each compound within the total face area of peaks of all the compounds in the reaction system.

In the present specification, the ratio between the compound represented by formula (II) and the total of the compound represented by said formula (II) and the compounds represented by formula (III) is used to evaluate purity. It will be noted that the aforesaid ratio is expressed as (II)/((II)+(III)).

When the present process is used, $0.95 \leq (II)/((II)+(III)) < 1$. A higher purify of $0.99 \leq (II)/((II)+(III)) < 1$ is preferable.

So long as the peaks of compound (II) and compound (III) can be separated, the gradient is not particularly limited, but method B presented below can be mentioned by way of example.

"Reaction byproducts" include the reaction solution and reaction slurry during reaction and after completion of reaction, the organic layer and aqueous layer after liquid separation and extraction, the products after purification, etc.

A formulation low in impurities can be produced by preparing the formulation using a compound represented by formula (II) obtained by means of the present invention.

Namely, the present invention makes it possible to obtain a pharmaceutical composition containing a compound represented by formula (II) as an active ingredient and furthermore containing compounds represented by formula (III), wherein the quantity of compounds represented by formula (III) is 0.2 weight percent or less of the quantity of compound represented by said formula (II). Even more preferably, the quantity of compounds represented by said formula (III) is 0.15 weight percent or less of the quantity of compound represented by said formula (II).

It should be noted that compounds represented by formula (II) and compounds represented by formula (III) as used in such a pharmaceutical composition include salts and solvates.

Examples of "salts" include sodium salt, lithium salt, potassium salt, calcium salt and other inorganic base salts.

Examples of "solvates" include hydrates, alcoholates, etc. of the compounds or of salts thereof. For instance, monohydrates, dihydrates, monoalcoholates, dialcoholates, etc. of the compounds air salts thereof may be mentioned as examples.

Embodiment Example 1

Production Method for Ospemifene (Chemical formula 25)

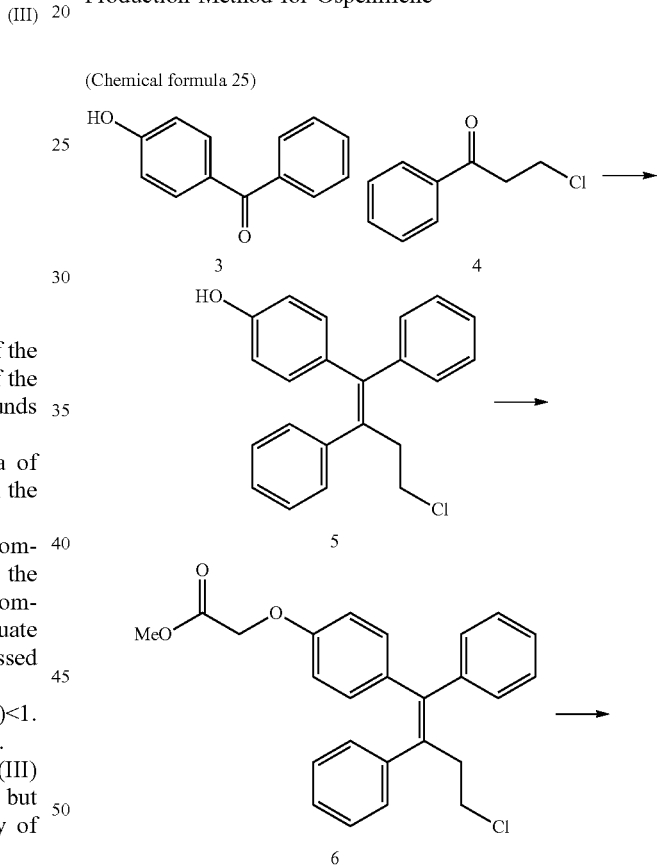

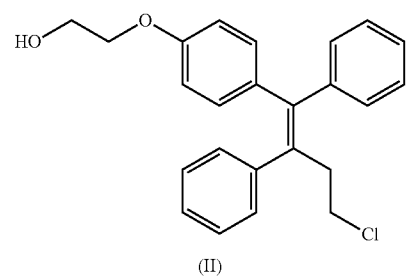
(II)

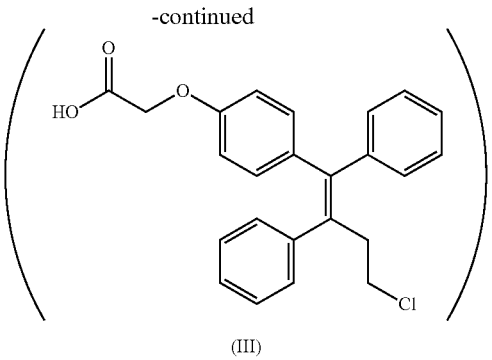

(III)

Process 1-1 Synthesis of Compound 5

Under a nitrogen atmosphere, compound 3 (2.97 g, 15 mmol), compound 4 (2.53 g, 15 mmol), zinc (3.73 g, 57 mmol) and potassium chloride (4.25 g, 57 mmol) were suspended in 2-methyl tetrahydrofuran (15 mL). After reducing pressure, nitrogen substitution was repeated 5 times. Titanium tetrachloride (3.14 ml, 28.5 mmol) was added over the course of 30 minutes at 0 degrees, after which agitation was performed for 20 minutes at room temperature and for 2 hours at 50 degrees. After leaving to cool, concentrated hydrochloric acid (6.1 g) water (16 mL) was added, insolubles were filtered out, and extraction was performed with ethyl acetate. The organic layer was washed with water and saturated table salt water, and was then dried with anhydrous sodium sulfate. The solvent was distilled off under reduced pressure and a portion (331 mg) of the obtained residue (7.18 g) was sampled. This was purified column chromatography to obtain compound 5 (160 mg, Z:E=5.7:1). Methanol-water was added to the remainder to precipitate out solids, after which a crude product (4.98 g) of compound 5 was obtained by filtering off. (Quantitated value: 69.2%, Z:E 5.7:1)

Process 1-2 Synthesis of Compound 5

Under a nitrogen atmosphere, compound 3 (14.87 g, 75.0 mmol), compound 4 (12.65 g, 75.0 mmol) and zinc (18.64 g, 285 mmol) were suspended in 2-methyl tetrahydrofuran (149 mL). After reducing pressure, nitrogen substitution was repeated 5 times. Titanium tetrachloride (26.48 mg, 140 mmol) was added over the course of approximately 2 hours at 0 degrees, after which agitation was performed for 3 hours at 50 degrees. After leaving to cool, concentrated hydrochloric acid (30.34 g) water (80.01 g) was added, insolubles were filtered out, and extraction was performed with ethyl acetate. The organic layer was washed 3 times with water to obtain an organic layer (359.9 g). This organic layer was divided into portions, and the solvent from one portion (119.69 g) was distilled off. Methanol was added to the residue, and the operation of distilling solvent off under reduced pressure was repeated 2 times. Methanol (33 mL)/water (13.5 mL) was then added, the solids were precipitated out, and filtration was then performed to obtain a crude product (4.599 g) of compound 5. (Quantitative value: 46.6%, Z:E=19:1)

Process 2-1 Synthesis of Compound 6

Crude product (4.98 g) of compound 5 was dissolved in N,N-dimethyl formamide (25 mL), methyl 2-bromoacetate (1.69 mL, 17.9 mmol) and potassium carbonate (3.08 g, 22.31 mmol) were added, and agitation was performed for 1 hour at room temperature. Water was added to the reaction liquid and extraction was performed with ethyl acetate. The organic layer was washed with water and saturated table salt water and then dried with anhydrous sodium sulfate. The solvent was distilled off under reduced pressure to obtain a crude product (6.05 g) of compound 6.

$^1$H-NMR (CDCl$_3$) δ: 2.92 (t, J=7.4 Hz, 2H), 3.41 (t, J=7.4 Hz, 2H), 3.75 (s, 3H), 4.50 (s, 2H), 6.55 (d, J=8.6 Hz, 2H), 6.80 (d, J=8.6 Hz, 2H), 7.08-7.43 (m, 10H).

Process 2-2 Synthesis of Compound 6

Compound 5 (200 mg, 0.597 mmol, Z:E=20:1) was dissolved in N,N-dimethyl formamide (1 mL), adding methyl 2-bromoacetate (67.8 μL, 0.717 mmol) and potassium carbonate (99 mg, 0.717 mmol) thereto and agitating for 2 hours at room temperature. Water was added to the reaction liquid and extraction was performed with ethyl acetate. The organic layer was washed with water and saturated table salt water and then dried with anhydrous sodium sulfate. The solvent was distilled off under reduced pressure and the residue was purified by column chromotography to obtain compound 6 (243 mg, quant, Z:E=20:1).

$^1$H-NMR (CDCl$_3$) δ: 2.92 (t, J=7.4 Hz, 2H), 3.41 (t, J=7.4 Hz, 2H), 3.75 (s, 3H), 4.50 (s, 2H), 6.55 (d, J=8.6 Hz, 2H), 6.80 (d, J=8.6 Hz, 2H), 7.08-7.43 (m, 10H).

Process 3-1 Synthesis of Compound (II) (Ospemifene)

Tetrahydrofuran (2.5 mL) was added to lithium chloride (104.2 mg. 2.458 mmol) and potassium borohydride (132.6 mg, 2.458 mmol), agitating for 2.5 hours to form a slurry. Chlorotrimethyl silane (31 μL, 0.245 mmol) was added to the slurry and compound 6 (1.00 g, 2.458 mmol) dissolved in tetrahydrofuran (4.5 mL) was added dropwise at room temperature, agitating for 3.5 hours.

The reaction liquid was analyzed by HPLC (measurement method B).

Compound (II) HPLC area percentage: 98.13%, retention time: 29.4 minutes

Compound (III) HPLC area percentage: 0.03% retention time: 38.2 minutes $(II)/((II)+(III))=0.997$ Acetone (724 μL, 9.802 mmol) and 1 mol/L hydrochloric acid were added to the reaction liquid and extraction was performed with ethyl acetate. The organic layer was washed with water and 5% table salt water and was then concentrated. Methanol was added to the concentrated residue and water was added dropwise to induce crystallization. The crystals were filtered off and washed with 70% methanol-water to obtain compound (II) (0.82 g, yield: 88%).

Process 3-2 Synthesis of Compound (II) (Ospemifene)

Compound (II) was obtained, using lithium chloride (1.0 eq) and potassium borohydride (1.0 eq) instead of the lithium chloride (1.0 eq), potassium borohydride (1.0 eq) and chlorotrimethyl silane (0.1 eq) in the above process 3-1.

HPLC Analysis of Reaction Liquid (Measurement Method A)

Compound (II) HPLC area percentage: 96.35%, retention time: 20.6 minutes

The method is otherwise the same as process 3-1 above. (Yield: 89.8)

Process 3-3 Synthesis of Compound (II) (Ospemifene)

Compound (II) was obtained using lithium borohydride (0.6 eq) instead of the lithium chloride (1.0 eq), potassium borohydride (1.0 eq) and chlorotrimethyl silane (0.1 eq) in the above process 3-1.

HPLC Analysis of Reaction Liquid (Measurement Method A)
Compound (II) HPLC area percentage: 98.27%, retention time. 17.66 minutes
The method is otherwise the same as process 3-1 above. (Yield: 92.4%)
Process 3-4 Synthesis of Compound (II) (Ospemifene)
Compound (II) was obtained using lithium borohydride (1.0 eq) and calcium chloride (0.25 eq) instead of the lithium chloride (1.0 eq), potassium borohydride (1.0 eq) and chlorotrimethyl silane (0.1 eq) in the above process 3-1.
HPLC Analysis of Reaction Liquid (Measurement Method A)
Compound (II) HPLC area percentage: 96.03%, retention time: 20.48 minutes
The method is otherwise the same as process 3-1 above.
Process 3-5 Synthesis of Compound (II) (Ospemifene)
Compound (II) was obtained using lithium borohydride (1.0 eq) and borane-THF complex (0.1 eq) instead of the lithium chloride (1.0 eq), potassium borohydride (1.0 eq) and chlorotrimethyl silane (0.1 eq) in the above process 3-1.
HPLC Analysis of Reaction Liquid (Measurement Method B)
Compound (II) HPLC area percentage: 98.62%, retention time: 29.36 minutes
Compound (III) Below detection limit.
The method is otherwise the same as process 3-1 above.
Process 3-6 Synthesis of Compound (II) (Ospemifene)
Compound (II) was obtained using lithium borohydride (1.0 eq) and chlorotrimethyl silane (0.1 eq) instead of the lithium chloride (1.0 eq), potassium borohydride (1.0 eq) and chlorotrimethyl silane (0.1 eq) in the above process 3-1.
HPLC Analysis of Reaction Liquid (Measurement Method B)
Compound (II) HPLC area percentage: 98.77%, retention time: 29.25 minutes
Compound (III) Below detection limit.
The method is otherwise the same as process 3-1 above.
Process 3-7 Synthesis of Compound (II) (Ospemifene)
Compound (II) was obtained using lithium borohydride (1.0 eq) instead of the lithium chloride (1.0 eq), potassium borohydride (1.0 eq) and chlorotrimethyl silane (0.1 eq) in the above process 3-1.
HPLC Analysis of Reaction Liquid (Measurement Method B)
Compound (II) HPLC area percentage: 97.63%, retention time: 29.29 minutes
Compound (III) HPLC area percentage: 0.79%, retention time: 38.03 minutes $(II)/((II)+(III))=0.991$ The method is otherwise the same as process 3-1 above.
HPLC measurements were performed under the following conditions.
(Measurement Method A)
Column: Symmetry C18, 5 μm (3.9×150 mm)
Flow rate: 1.0 mL/minute
UV detection wavelength: 235 nm
Column temperature: 40° C.
Mobile phase: (A)=aqueous solution containing 0.03% acetic acid/acetonitrile=80/20; (B)=acetonitrile
Gradient: 40% solvent (B) was maintained for 31 minutes, a linear gradient of 40% to 70% solvent (B) was performed for 2 minutes, 70% solvent (B) was maintained for 16 minutes, a linear gradient of 70% to 95% solvent (B) was performed for 3 minutes, and 95% solvent (B) was maintained for 10 minutes.

(Measurement Method B)
Column: Symmetry C8, 3.5 μm (4.6×150 mm)
Flow rate: 1.0 mL/minute
UV detection wavelength: 235 nm
Column temperature: 25° C.
Mobile phase: (A)=aqueous solution containing 0.03% acetic acid acetonitrile=80/20; (B)=acetonitrile
Gradient: 37.5% solvent (B) was maintained for 10 minutes and a linear gradient of 37.5% to 87.5% solvent (B) was performed for 80 minutes.

INDUSTRIAL APPLICABILITY

Ospemifene can be efficiently produced using the present invention.

The invention claimed is:
1. A production method for a compound represented by the formula (II):

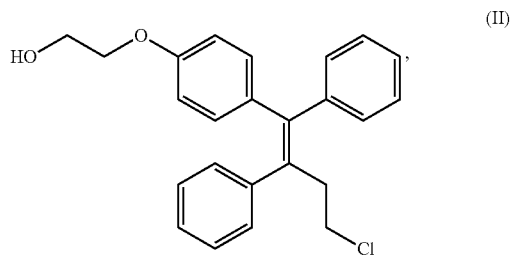 [SMILES: OCCOc1ccc(/C(=C(/CCCl)c2ccccc2)c2ccccc2)cc1]

comprising the step of reducing a compound represented by the formula (I):

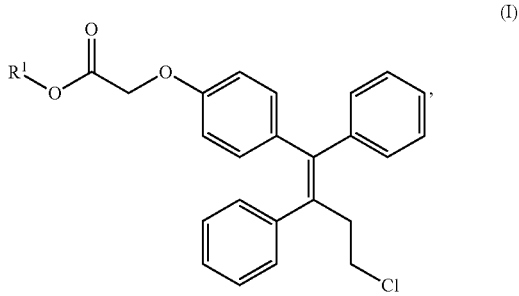

wherein $R^1$ is a substituted or unsubstituted alkyl, in the presence of lithium borohydride, tetrahydrofuran, and trimethylsilyl chloride.

2. A production method as set forth in claim 1, wherein the lithium borohydride is formed in the reaction system.

3. A production method as set forth in claim 2, wherein the lithium borohydride is formed in the reaction system by reacting potassium borohydride with lithium chloride.

4. A production method as set forth in claim 1 wherein the reaction is performed in the presence of borane.

5. A production method as set forth in claim 1 wherein $R^1$ is methyl.

6. A production method as set forth in claim 1 wherein the ratio between the compound represented by the formula (II):

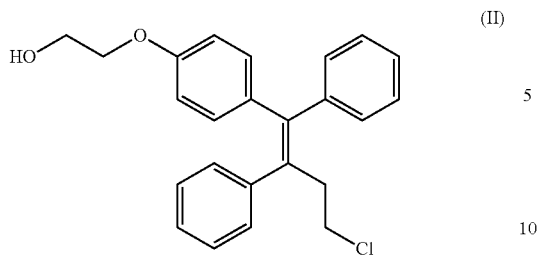
(II)
and the total of the compound represented by said formula (II) and the compound represented by the formula (III):
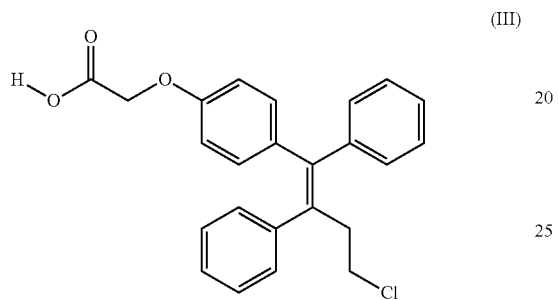
(III)
is $0.95 \leq (II)/((II)+(III)) < 1$.
* * * * *